United States Patent [19]

Fritscher et al.

[11] Patent Number: 4,552,722
[45] Date of Patent: Nov. 12, 1985

[54] APPARATUS FOR THE HOT GAS CORROSION OF SAMPLES OF MATERIAL

[75] Inventors: Klaus Fritscher, Cologne; Horst Gedanitz, Leverkusen, both of Fed. Rep. of Germany

[73] Assignee: DeutscheForschungs -und Versuchsanstalt fur Luft -und Raumfahrt e.V., Cologne, Fed. Rep. of Germany

[21] Appl. No.: 502,553

[22] Filed: Jun. 9, 1983

[30] Foreign Application Priority Data

Jun. 12, 1982 [DE] Fed. Rep. of Germany ....... 3222182

[51] Int. Cl.⁴ .............................................. G01N 17/00
[52] U.S. Cl. ........................................... 422/53; 436/6
[58] Field of Search ................... 422/53, 78, 199, 248; 156/620; 436/6, 155, 157; 73/61.2

[56] References Cited

U.S. PATENT DOCUMENTS

| | | | |
|---|---|---|---|
| 2,532,257 | 11/1950 | Kirshenbaum et al. | 422/53 |
| 3,080,747 | 3/1963 | Kerst | 73/61.2 |
| 3,098,720 | 7/1963 | Neffenger | 422/53 |
| 3,141,324 | 7/1964 | Boies et al. | 73/61.2 |
| 3,936,273 | 2/1976 | Powell | 422/53 |
| 3,957,440 | 5/1976 | Aussieker | 422/53 |
| 3,960,496 | 6/1976 | Schieber | 422/53 |

OTHER PUBLICATIONS

F. A. Champion, Corrosion Testing Procedures, Second Edition, 1965, pp. 212-219.

Primary Examiner—Barry S. Richman
Assistant Examiner—Lynn M. Kummert
Attorney, Agent, or Firm—Birch, Stewart, Kolasch & Birch

[57] ABSTRACT

A sample of material which is to be exposed to a hot gas corrosion is suspended in a pipe and is irradiated with heat radiation through parabolic mirrors through the pipe. Beneath the sample of material, there is found a thermocouple element which is also arranged along the focusing line. The substance stimulating corrosion is provided in a crucible furnace which is heated separately. Through a gas connection, gas or steam is supplied in order to generate the atmosphere stimulating corrosion in the pipe. The variations in weight of the sample of material are continuously measured with a balance.

11 Claims, 3 Drawing Figures

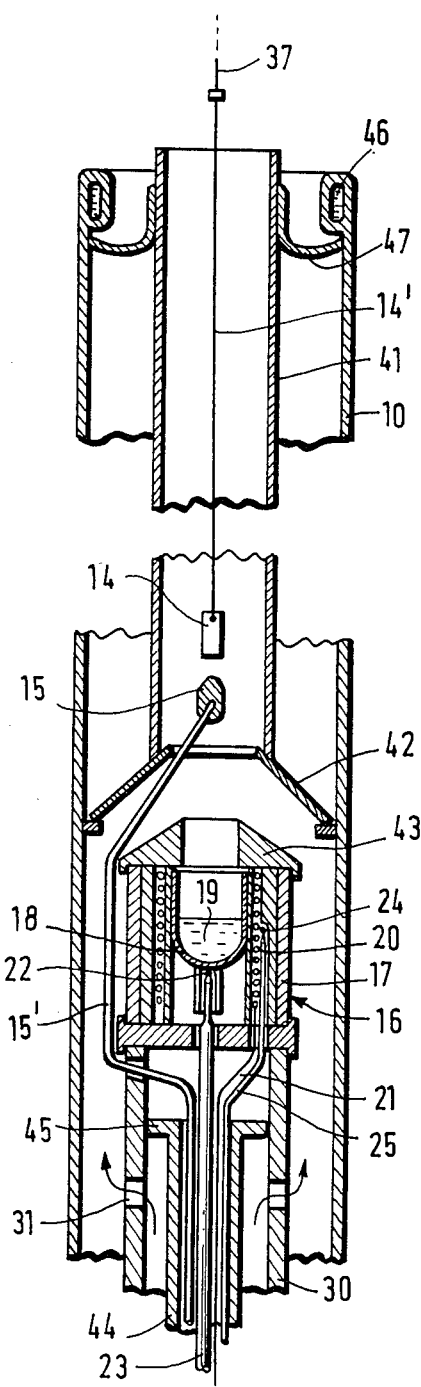

APPARATUS FOR THE HOT GAS CORROSION OF SAMPLES OF MATERIAL

BACKGROUND OF THE INVENTION

This invention relates to an apparatus for the hot gas corrosion of samples of material and, more specifically, to an apparatus having a pipe for taking up the sample of material, a steam and/or gas source, which is attached to the pipe, and a means for the purpose of evaporating a substance stimulating corrosion.

Turbines are often operated in an atmosphere which stimulates corrosion and which contains, for example, sea salt. When the turbine blades cool down after the turbine has been switched off, the substance stimulating corrosion (e.g., $Na_2SO_4$) is deposited on the turbine blades in a concentrated form. When the turbine blades reheat afterwards, the corroding material becomes effective.

In order to examine the corrosive effect of various corroding substances on different samples of material, an apparatus has been developed in the prior art, which apparatus has a horizontal pipe for taking up a sample of material. Steam-saturated air is conducted through the pipe while, at the same time, a substance stimulating corrosion is fed through the pipe wall in a specific concentration. During the course of the experiment, the pipe is heated in a controlled form evenly over its entire length. This known apparatus has the disadvantage that the sample of material to be corroded is arranged lying in the pipe and is, thus, not evenly corroded from all sides. Moreover, the heating-up of the sample of material is coupled with the temperature of the pipe. As the sample of material in the pipe is not arranged concentrically, different areas of the surface of the sample of material have dissimilar temperatures.

The underlying object of the present invention is to provide an apparatus of the kind named by way of introduction, which apparatus makes possible a purposeful and uniform heating and corrosion of the surface of a sample of material and, thus, provides better information about the corrosive behavior of the material.

SUMMARY OF THE INVENTION

In order to achieve this object of the present invention, the sample of material to be corroded is arranged in an upright pipe in a freely suspended manner. Beneath the sample of material, there is provision for a heated crucible for receiving the substance to be evaporated for stimulating corrosion, and outside the pipe there is arranged a radiant heat source, the radiation of which is directed through the wall of the pipe which is permeable to the radiation, at least to some extent, onto the sample of material. Likewise, the evaporated corrosive stimulating substance deposits on the sample.

As the sample of material in the pipe is freely suspended, it does not touch or contact any other surface. The sample of material is, therefore, exposed to heating and corrosion on its whole surface. The heating of the sample of material takes place to a substantial extent through radiant heat so that the sample of material heats essentially to a greater extent than does the pipe. The radiation is concentrated onto the area of the central axis of the pipe where the sample of material is found.

A thermocouple element, whose diameter essentially corresponds to that of the sample of material, is preferably arranged beneath the sample of material. This thermocouple element is also found on the central axis of the pipe. As the diameter of the thermocouple element is of approximately the same size as the diameter of the sample, the same radiant heat is supplied to the thermocouple element per unit of length as to the sample. In this manner the amount of heat, which is supplied to the sample, can be determined without contact.

According to a preferred embodiment of the invention, the sample of material is secured on a pull element which is suspended on a weighing device. With the weighing device, the variations in weight of the sample, which are conditional upon corrosion, can be measured while the experiment is in progress without the experiment having to be interrupted. Due to the continuous determination of weight, it is possible not only to determine the advance of corrosion by final inspection but to observe it continuously during the whole course of the experiment. The advance of corrosion is divided, for example, into an incubation period with little weight effect, a period which follows the incubation period and during which a covering layer is formed, with greater weight gain lessening parabolically over a period of time, and finally a layer-forming period which accelerates greatly and in which a non-protecting layer is produced. Through determination and analysis of the respective periods, the corrosion resistance of a material can be determined more exactly than before.

The radiant heating device advantageously has at least one mirror focused onto the axis of the pipe. Preferably, there are provided several mirrors which are arranged spatially with respect to the periphery of the pipe and which are focused all together onto the axis of the pipe. In this manner a simultaneous heating of the whole peripheral area of the sample results, where the temperature of the sample can be essentially greater than the temperature of the pipe.

While in the known testing apparatus the corroding material is continuously introduced into the pipe, in the case of the apparatus according to the present invention, the corrosion causing material is found inside the crucible in the pipe. The crucible is heated independently of the heating of the sample material in order to effect the evaporation of the material which stimulates corrosion. According to a preferred embodiment of the invention, the crucible, which is impermeable to radiation, is arranged along the axis of the pipe with its peripheral wall at a predetermined distance from the focusing axis of the radiant heating device. With this arrangement, the crucible wall is certainly hit by the radiation of the radiant heating device; however, in the case of the crucible, there follows a much lower heating by radiation than in the case of the sample of material. The heating of the sample of material and the heating of the crucible can, therefore, be controlled independently of each other. To this purpose the crucible has a controllable electric heating device with at least one thermocouple element built into the crucible wall.

If several materials for stimulating corrosion are to be introduced to act on the sample of material at the same time, several crucibles can be arranged in the pipe, one beneath the other, each being controlled separately in terms of temperature. The crucible which has the higher temperature is positioned a shorter distance from the sample. In this manner a premature condensation of the evaporated media stimulating corrosion is prevented before the sample is reached. The media are directed through the stack effect of the pipe upwards to the sample. Assisting this is a stream of gas, which is as constant as possible and which also contains corrosive constituents (e.g., $SO_2$ and/or $H_2O$) and can be blown into the pipe from below. The crucible, which is arranged in the pipe, herewith serves as an obstacle at the same time in order to swirl the upward, laminar gas flow whereby there follows a good intermixture in the upward gas stream of the evaporating corrosive agent.

In order to intensify the effect of stimulating corrosion, according to an advantageous embodiment of the invention, a tube, which is permeable to radiation from a radiant heat source and which surrounds the sample of material, is arranged in the pipe. Between the crucible and the lower end of the tube above the crucible, there is arranged a conical guide ring which extends between the tube and the pipe. As the sample has, in general, essentially smaller radial dimensions than the crucible, it is arranged in the narrower tube. By means of the conical guide ring, a situation is reached whereby the whole atmosphere stimulating corrosion in a laminar flow is conducted into the tube which is narrower than the pipe. In this manner there results a better utilization and concentration of the flow stimulating corrosion onto the sample.

Between the tube and the pipe, there can be arranged a collecting channel for condensate above the sample of material in the range of a cooling device. Condensate, which forms with the action of the cooling device, is thereby prevented from falling down in the pipe.

An insulating guard ring, which leaves the crucible opening free, with inclined outer surface, is advantageously arranged over the crucible wall. The guard ring makes it difficult for surface portions, which have loosened from the sample of material, to fall into the crucible which is open at the top. At the same time, it serves as a heat insulator between the crucible and the sample of material.

When the thermocouple element, which is arranged beneath the sample along the central axis of the pipe, has a conical point pointing upwards, the thermocouple element also serves to reject material particulate, which may fall down, from the crucible opening.

BRIEF DESCRIPTION OF THE DRAWINGS

In the following, preferred embodiments of the invention are explained in greater detail with reference to the drawings. These embodiments are intended to be illustrative of the present invention and not limiting thereof.

FIG. 3 shows a diagrammatic longitudinal section through a second embodiment of the apparatus of the present invention.

DETAILED DESCRIPTION

Figure 1:
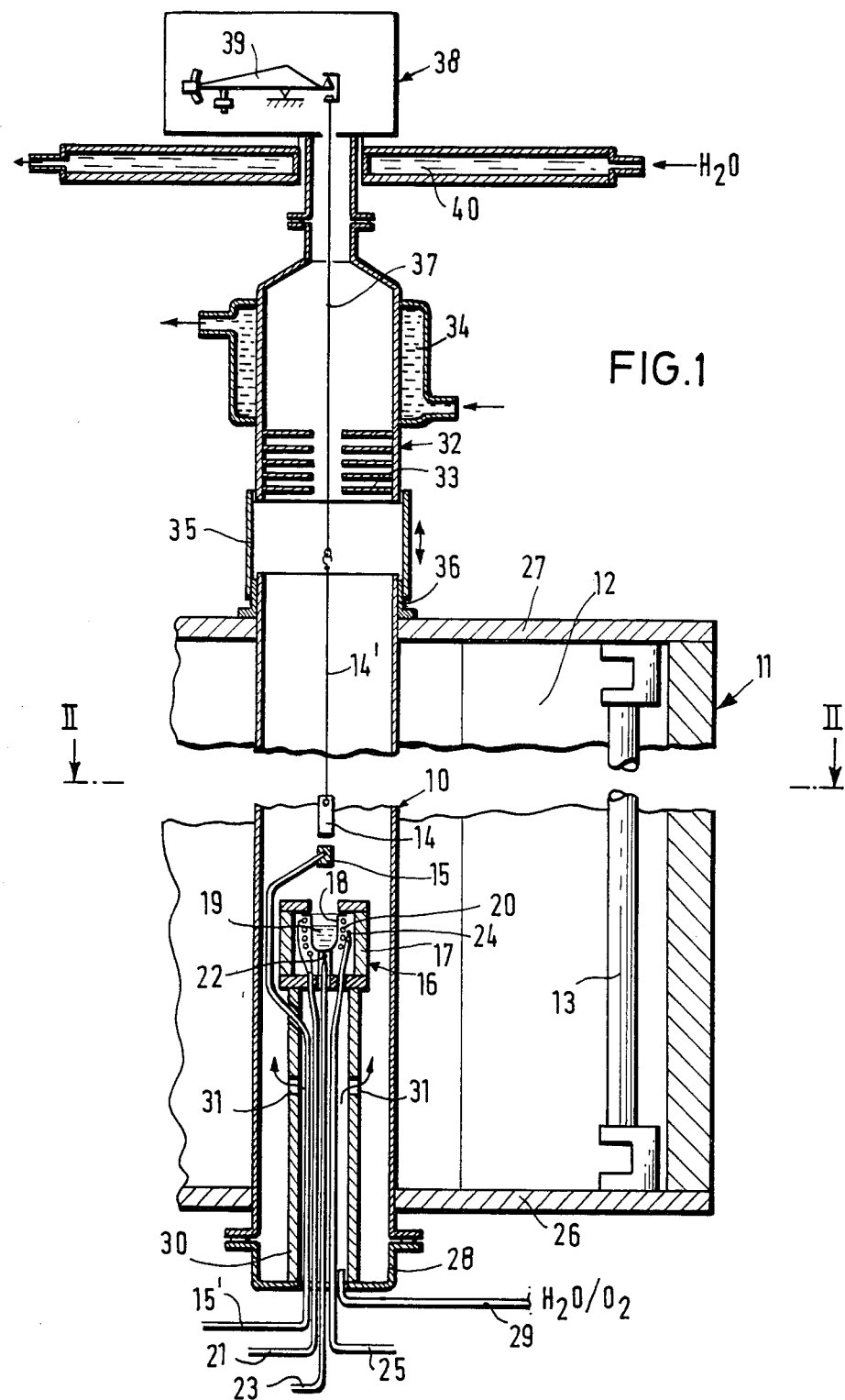
FIG. 1 shows a diagrammatic longitudinal section through a first embodiment of the apparatus.
Figure 2:
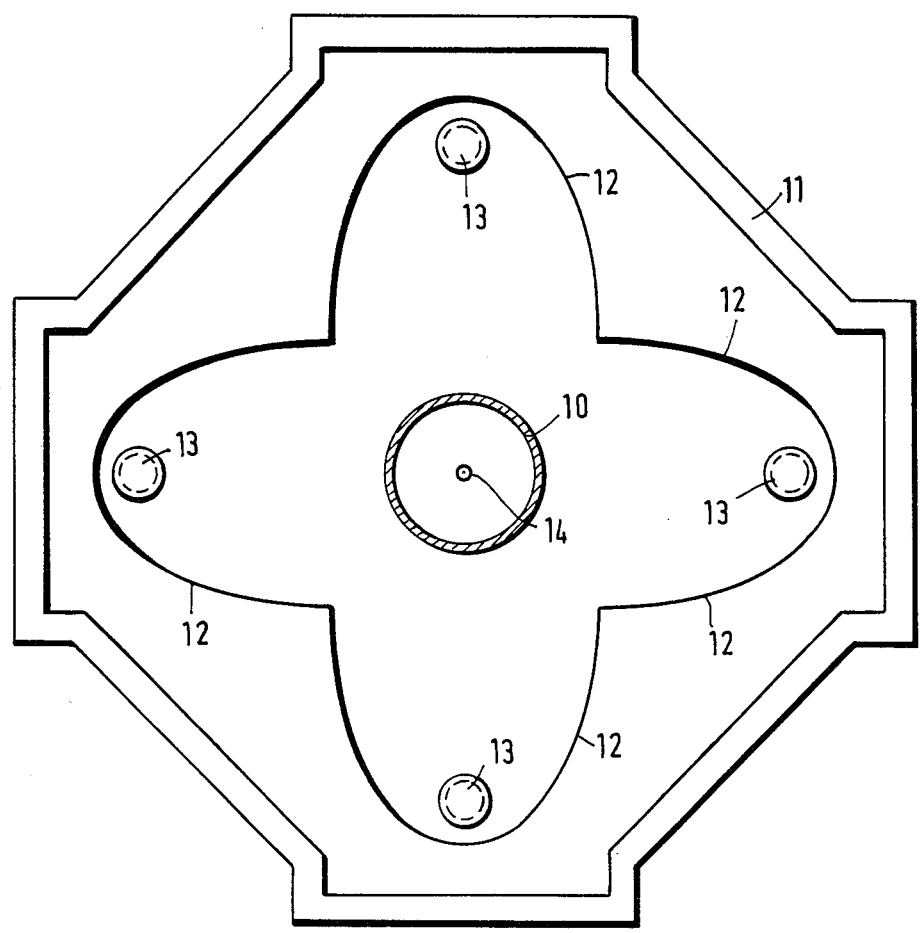
FIG. 2 shows a section along the line II—II of FIG. 1.

In the exemplary embodiment of FIGS. 1 and 2, a cylindrical pipe 10 having a vertical pipe axis is arranged concentrically in a housing 11 which, in top view, is star-shaped. In the housing 11, there are found four parabolic mirrors 12 which are arranged in the manner of a cross. In each parabolic mirror 12, there is arranged a bar-shaped heating element 13, the radiation of which is focused in a linear manner onto the axis of the pipe 10. The pipe 10 is made of quartz glass or other material which is permeable to heat radiation, for example, transluscent $Al_2O_3$.

Along the axis of the pipe 10, the sample of material 14 is suspended on a thread 14' of Pt-Ir. The sample 14 is cylindrical and has a low bulk. When the heating devices 13 are switched off, the sample 14 quickly radiates the specific heat due to its low bulk. This corresponds to the cooling of turbine blades when a turbine is switched off.

Immediately under the sample of material 14, there is found a thermocouple element 15 which is also arranged along the axis of the pipe 10, the diameter of which is as large as that of the sample of material 14 so that the thermocouple element 15, which is also arranged along the caustic line of the parabolic mirror 12, is heated in the same way as the sample of material 14. The thermocouple element 15 is connected by way of lines 15' with a control device (not shown) which is arranged outside the pipe.

Below the thermocouple element 15, there is arranged, likewise coaxially to the axis of the pipe 10, the crucible furnace 16, the side wall 17 of which has an essentially greater diameter than the sample of material 14 and the thermocouple element 15. In the configuration, however, an annulus for the ascent of gases is kept free between the side wall 17 and the wall of the pipe 10. The crucible furnace 16 has a crucible 18, which only opens towards the top and which is arranged coaxially in the pipe 10. The crucible is made of corrosion-proof material and contains a substance 19 for stimulating corrosion. Between the crucible 18 and the wall 17, there is found a heating coil 20, which is connected to a source of current by way of lines 21 led out from the pipe 10. In the floor wall of the crucible 18, there is provision for a further thermocouple element 22, the lines 23 of which are also led out from the pipe 10. Finally a third thermocouple element 24 is arranged on the heating coil 20. The lines 25 of this thermocouple element are connected to the control and regulating device.

The pipe 10 is passed through openings in the floor wall 26 and the upper wall 27 of the housing 11 in a sealed manner. Onto the lower end of the pipe 10, there is attached a cap 28 which has openings for the penetration of the lines 15', 21, 23 and 25 and which also has a gas connection 29. The lines 15', 21, 23, and 25 and the gas connection 29 lead through the floor wall of the cap 28 into the interior of a tubular holding device 30, on the upper end of which the crucible furnace 16 is arranged. The holding device 30 has lateral openings 31 for the escape of the gases supplied from the gas connection 29.

Onto the upper end of the pipe 10 there is mounted, outside the housing 11, a tubular head piece 32 which has a labyrinth seal 33 and a water-jacketed cooling jacket 34. On the lower end of the head piece 32, there is found a sliding ring 35 which slides on a seal 36 on the outside of the pipe 10 in order to be able to alter the height of the head piece 32 as desired. Through the head piece 32, there passes coaxially a wire 37 having secured to its lower end thread 14' which carries the sample 14. The upper end of the wire 37 is secured on a balance 39 which is arranged in a housing 38 and with which the variations in weight of the sample 14 are continuously recorded. Beneath the housing 38, there is found a cooling screen 40 which is cooled with water in order to prevent the balance 39 from heating.

The exemplary embodiment of FIG. 3 largely resembles that of FIGS. 1 and 2 so that in the following only the differences are explained.

According to FIG. 3, there is coaxially arranged in the pipe 10 a tube 41 which is made, for example, of a transluscent material such as Al₂O₃. The diameter of the tube 41 is approximately half as great as the diameter of the pipe 10. The lower end of the tube 41 is found between the thermocouple element 15 and the crucible furnace 16. From the lower end of the tube 41, there extends a conical guide ring 42 inclined outwards and downwards as far as the wall of the pipe 10. This guide ring 42 forms a hood for the purpose of concentrating the flow of gases and vaporized materials ascending in the pipe 10 and for the purpose of conducting this flow into the tube 41.

The wall of the crucible furnace 16 is covered with a guard ring 43 which, on the one hand, forms a radiation protection in order to prevent the radiation, issuing from the heating elements 13, from affecting the substance 19 for stimulating corrosion in the crucible 18 and which, on the other hand, forms a protective hood for the purpose of keeping falling sample particulate away from the bur of the crucible 18. In order to divert the falling particulate material outwards, the upper side of the guard ring 43 is constructed in an inclined manner.

The thermocouple element 15 has a platinum casing for protecting against the corrosive agent. It is constructed with a conical point at its upper end in order to keep loosening layers of the sample away from the crucible 18. The lower end of the thermocouple element 15 is rounded off in the shape of a cupola so as not to interfere with the laminar flow of the ascending atmosphere.

In the tubular holding device 30, there is found a protective pipe 44 through which the lines 15', 21, 23 and 25 run. In the annulus between the protective pipe 44 and the holding device 30, there flows the gas which leaves this annulus through the lateral openings 31. At the upper end of the protective pipe 44, there is found an annular flange 45 which stands out towards the outside and which closes the annulus above the openings 31.

At the upper end of the pipe 10, there is arranged a cooling device 46 in the form of a cooling ring. Below the cooling device 46, there is found the collecting channel 47 for collecting the forming condensate. If, for example, Na₂SO₄ is used as a medium for stimulating corrosion, the following reaction takes place when there is condensation:

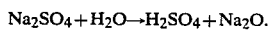

$$Na_2SO_4 + H_2O \rightarrow H_2SO_4 + Na_2O.$$

The resultant sulphuric acid is deposited in the collecting channel 47 with the aid of the cooling device 46, while Na₂O has a corrosive effect on the sample 14.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An apparatus for determining the corrosive effect of corrosion stimulating substances on selected material which comprises:
    (a) a means for freely suspending a sample of material to be corroded by a corrosive stimulating substance comprising an upright pipe having a central axis where the sample of material is found, the wall of said pipe being substantially permeable to radiation from a radiant heat source;
    (b) means for introducing a corrosive gas into said means for suspending said sample;
    (c) crucible means for receiving and evaporating said corrosive stimulating substance having a peripheral wall which is impermeable to radiation from a radiant heat source, said crucible means being positioned beneath said sample of material;
    (d) means for heating said sample of material comprising a radiant heat source located outside said pipe whereby radiation from said heat source is directed through said pipe wall onto said sample; and
    (e) means for heating said corrosive stimulating substance receiving and evaporating means.

2. The apparatus according to claim 1, wherein said means for heating said crucible comprises a controllable electric heating device with at least one thermocouple element therefor.

3. The apparatus according to claim 1, wherein said crucible is arranged on a tubular holding device through which said gas is supplied and which has lateral discharge openings below said crucible.

4. The apparatus according to claim 1, wherein over the peripheral wall of said crucible there is provided an insulating guard ring which leaves the crucible opening free and which has an inclined outer surface.

5. The apparatus according to claim 1, wherein said sample of material is cylindrical with the axis thereof extending in the direction of said central axis and beneath said sample of material there is provided a thermocouple element, the diameter of which substantially corresponds to the diameter of said sample of material.

6. The apparatus according to claim 5, wherein said thermocouple element has a conical point pointing upwards.

7. The apparatus according to claim 1, wherein said pipe includes a tube having a lower end, said tube having a wall which is permeable to radiant energy radiation and which surrounds said sample of material within said pipe and which further includes between said crucible and said lower end of said tube a conical guide ring which extends between said tube and said pipe.

8. The apparatus according to claim 7, further including a cooling device positioned above said suspended sample having a collecting channel for condensation located between said tube and said pipe.

9. The apparatus according to claim 1, wherein said radiant heat source comprises at least one mirror focused onto the axis of said pipe.

10. The apparatus according to claim 9, wherein said radiant heat source comprises several mirrors arranged spatially with respect to the periphery of said pipe and which are focused all together onto the axis of said pipe.

11. The apparatus according to claim 9, wherein said crucible is positioned on the axis of said pipe and said peripheral wall is at a predetermined distance from said central axis of said radiant heat source.

* * * * *